United States Patent
Marshall et al.

(10) Patent No.: US 9,271,696 B2
(45) Date of Patent: Mar. 1, 2016

(54) ULTRASOUND IMAGING SYSTEMS WITH BIAS CIRCUITRY AND METHODS OF MAKING AND USING

(71) Applicant: Boston Scientific SciMed, Inc., Maple Grove, MN (US)

(72) Inventors: John D. Marshall, Los Gatos, CA (US); Donald Masters, San Diego, CA (US); Gaylin Mildred Yee, Newark, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 425 days.

(21) Appl. No.: 13/623,647

(22) Filed: Sep. 20, 2012

(65) Prior Publication Data

US 2013/0079642 A1 Mar. 28, 2013

Related U.S. Application Data (60) Provisional application No. 61/538,007, filed on Sep. 22, 2011.

(51) Int. Cl.
*A61B 8/00* (2006.01)
*A61B 8/12* (2006.01)

(52) U.S. Cl.
CPC ... *A61B 8/12* (2013.01); *A61B 8/56* (2013.01); *A61B 8/445* (2013.01); *A61B 8/4461* (2013.01)

(58) Field of Classification Search
CPC .............. A61B 8/56; A61B 8/00; A61B 8/08
USPC ....................................... 600/463
See application file for complete search history.

(56) References Cited

U.S. PATENT DOCUMENTS

| | | | |
|---|---|---|---|
| 6,945,938 B2 | 9/2005 | Grunwald | |
| 7,246,959 B2 | 7/2007 | Nakatani | |
| 7,306,561 B2 | 12/2007 | Sathyanarayana | |
| 2004/0108789 A1* | 6/2004 | Marshall | 310/216 |
| 2006/0084875 A1 | 4/2006 | Knight | |
| 2006/0100522 A1 | 5/2006 | Yuan et al. | |
| 2006/0106320 A1 | 5/2006 | Barbato | |
| 2006/0173350 A1 | 8/2006 | Yuan et al. | |
| 2006/0253028 A1 | 11/2006 | Lam et al. | |
| 2007/0016054 A1 | 1/2007 | Cao et al. | |
| 2007/0038111 A1 | 2/2007 | Rehrig et al. | |
| 2007/0083119 A1* | 4/2007 | Adachi | A61B 8/12 600/437 |
| 2009/0163817 A1 | 6/2009 | Masters et al. | |
| 2011/0207995 A1* | 8/2011 | Snow et al. | 600/37 |

FOREIGN PATENT DOCUMENTS

WO WO 2009048339 A1 * 4/2009
WO WO 2009073752 A1 * 6/2009

* cited by examiner

*Primary Examiner* — Joel Lamprecht
(74) *Attorney, Agent, or Firm* — Lowe Graham Jones PLLC; Bruce E. Black (57) ABSTRACT

A medical imaging system includes an imaging device for inserting into a lumen of a catheter. The imaging device includes an ultrasound transducer and bias circuitry electrically coupled to the transducer for biasing the transducer. At least one communication line is coupled to both the ultrasound transducer and the bias circuitry and extends to a proximal end of the catheter. The at least one communication line transmits a transducer drive signal to the transducer and a charge signal to the bias circuitry. At least one inductive coupler is in communication with the at least one communication line. The transducer drive signal and the charge signal are both AC signals. The transducer drive signal has a transducer-drive-signal frequency and the charge signal has a charge-signal frequency that is different than the transducer-drive-signal frequency.

27 Claims, 7 Drawing Sheets

Fig. 10

ULTRASOUND IMAGING SYSTEMS WITH BIAS CIRCUITRY AND METHODS OF MAKING AND USING

CROSS-REFERENCE TO RELATED APPLICATIONS

This application claims the benefit under 35 U.S.C. §119 (e) of U.S. Provisional Patent Application Ser. No. 61/538, 007 filed on Sep. 22, 2011, which is incorporated herein by reference.

TECHNICAL FIELD

The present invention is directed to the area of imaging systems insertable into patients and methods of making and using the imaging systems. The present invention is also directed to imaging systems with bias circuitry for electrically biasing one or more transducers, as well as methods of making and using the bias circuitry, the one or more transducers, and the imaging systems.

BACKGROUND

Ultrasound devices insertable into patients have proven diagnostic capabilities for a variety of diseases and disorders. For example, intravascular ultrasound ("IVUS") imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety of diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor.

BRIEF SUMMARY

In one embodiment, a medical imaging system includes a catheter configured and arranged for insertion into an intravascular portion of a living being. The catheter has a distal end and a proximal end. An imaging device is configured and arranged for insertion into a lumen defined in the catheter. The imaging device is configured and arranged for imaging interior portions of the living being. The imaging device includes at least one ultrasound transducer and bias circuitry electrically coupled to the at least one transducer. The bias circuitry is configured and arranged to electrically bias the at least one transducer. At least one communication line is coupled to both the at least one ultrasound transducer and the bias circuitry and extends to the proximal end of the catheter. The at least one communication line is configured and arranged for transmitting a transducer drive signal to the at least one transducer, and also for transmitting a charge signal to the bias circuitry. At least one inductive coupler is in communication with the at least one communication line. The transducer drive signal and the charge signal are both AC signals. The transducer drive signal has a transducer-drive-signal frequency and the charge signal has a charge-signal frequency that is different than the transducer-drive-signal frequency.

In another embodiment, a medical imaging system includes a catheter configured and arranged for insertion into an intravascular portion of a living being. The catheter has a distal end and a proximal end. An imaging device is configured and arranged for insertion into a lumen defined in the catheter. The imaging device is configured and arranged for imaging interior portions of the living being. The imaging device includes at least one ultrasound transducer and bias circuitry electrically coupled to the at least one transducer. The bias circuitry is configured and arranged to electrically bias the at least one transducer. A control module is communicatively coupled with the imaging device. The control module is configured and arranged to generate a transducer drive signal and a charge signal. At least one communication line couples the control module to both the at least one ultrasound transducer and the bias circuitry. The at least one communication line is configured and arranged for transmitting the transducer drive signal and the charge signal to the imaging device. The transducer drive signal and the charge signal are both AC signals. A first rotating transformer is disposed between the control module and the at least one communication line. The first rotating transformer is configured and arranged to receive the transducer drive signal. A second rotating transformer is disposed between the control module and the at least one communication line. The second rotating transformer is configured and arranged to receive the charge signal.

In yet another embodiment, a method of intravascular ultrasound imaging with an image processing system includes transmitting an AC transducer drive signal from a pulse generator to at least one transducer. The AC transducer drive signal includes a plurality of frequencies within an imaging frequency band. The transducer drive signal is configured and arranged to cause the at least one transducer to transmit an acoustic signal. An AC charge signal is transmitted from the pulse generator to bias circuitry communicatively coupled to the at least one transducer. The AC charge signal includes a charge-signal frequency that does not overlap with the imaging band frequencies. The AC charge signal is converted to a DC charge signal. The DC charge signal is stored in a charge pump. A bias signal is transmitted to the at least one transducer. The bias signal is formed from the stored DC charge signal.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of imaging systems insertable into patients and methods of making and using the imaging systems. The present invention is also directed to imaging systems with bias circuitry for electrically biasing one or more transducers, as well as methods of making and using the bias circuitry, the one or more transducers, and the imaging systems.

Suitable intravascular ultrasound ("IVUS") imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,246,959; 7,306,561; and 6,945,938; as well as U.S. Patent Application Publication Nos. 2006/0100522; 2006/0106320; 2006/0173350; 2006/0253028; 2007/0016054; and 2007/0038111; all of which are incorporated herein by reference.

Figure 1:
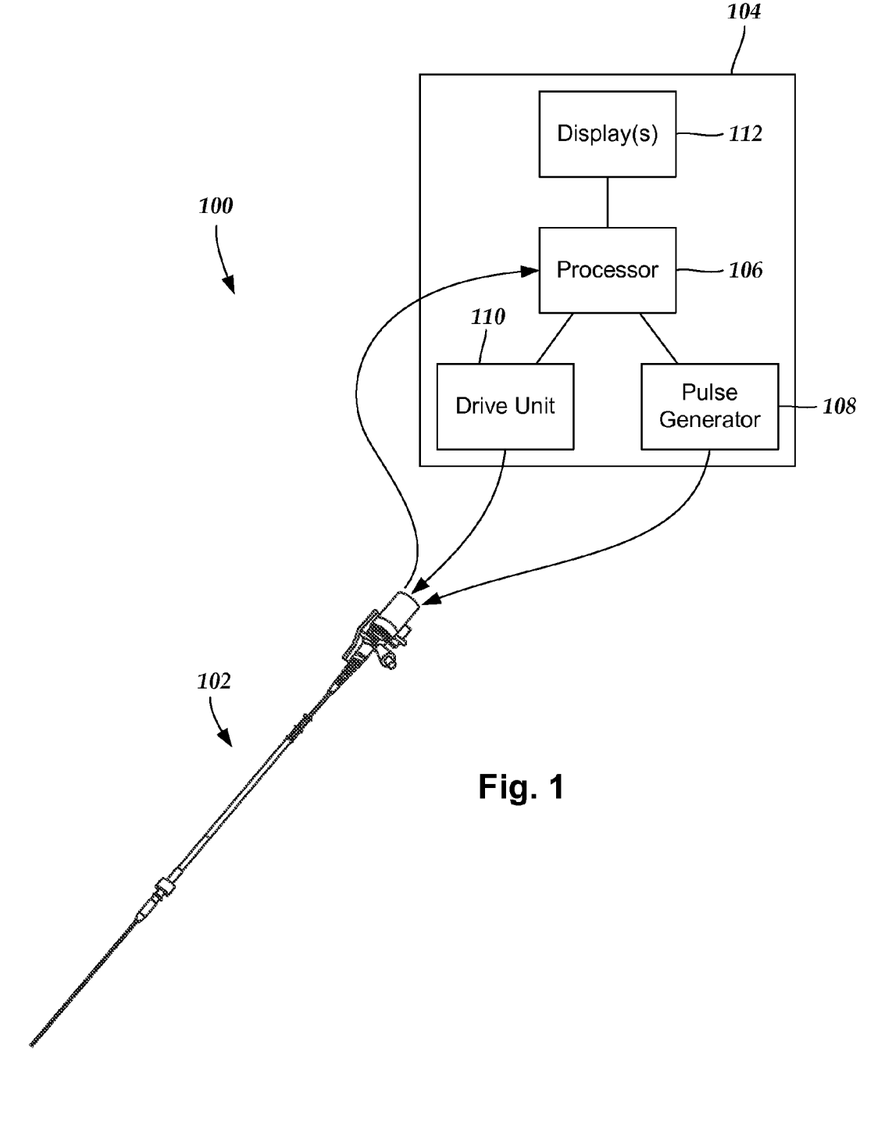
FIG. 1 is a schematic view of one embodiment of an imaging system suitable for insertion into a patient, the imaging system including a catheter and a control module, according to the invention.

FIG. 1 illustrates schematically one embodiment of an IVUS imaging system 100. The IVUS imaging system 100 includes a catheter 102 that is coupleable to a control module 104. The control module 104 may include, for example, a processor 106, a pulse generator 108, a drive unit 110, and one or more displays 112. In at least some embodiments, the pulse generator 108 forms electric pulses that may be input to one or more transducers (312 in FIG. 3) disposed in the catheter 102.

In at least some embodiments, mechanical energy from the drive unit 110 may be used to drive an imaging core (306 in FIG. 3) disposed in the catheter 102. In at least some embodiments, electric signals transmitted from the one or more transducers (312 in FIG. 3) may be input to the processor 106 for processing. In at least some embodiments, the processed electric signals from the one or more transducers (312 in FIG. 3) can be displayed as one or more images on the one or more displays 112. For example, a scan converter can be used to map scan line samples (e.g., radial scan line samples, or the like) to a two-dimensional Cartesian grid to display the one or more images on the one or more displays 112.

In at least some embodiments, the processor 106 may also be used to control the functioning of one or more of the other components of the control module 104. For example, the processor 106 may be used to control at least one of the frequency or duration of the electrical pulses transmitted from the pulse generator 108, the rotation rate of the imaging core (306 in FIG. 3) by the drive unit 110, the velocity or length of the pullback of the imaging core (306 in FIG. 3) by the drive unit 110, or one or more properties of one or more images formed on the one or more displays 112.

Figure 2:
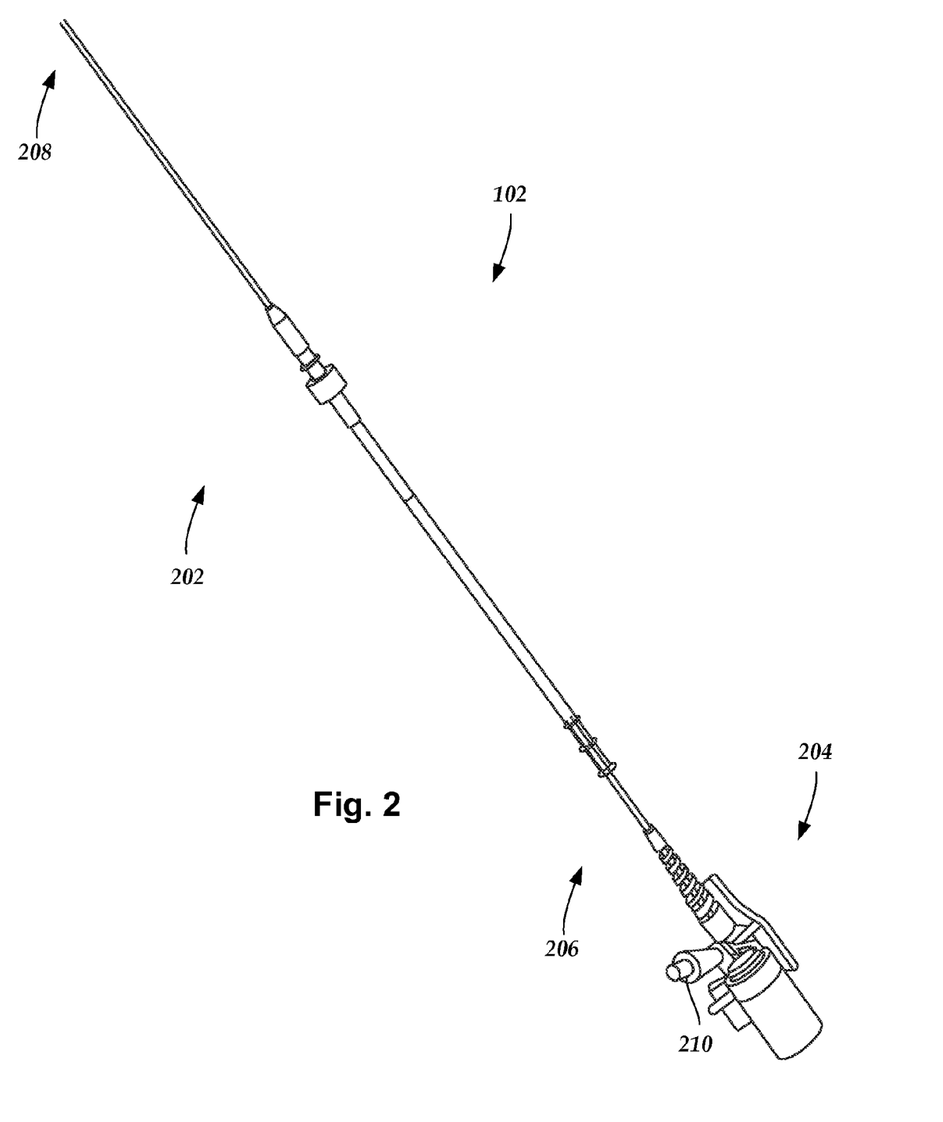
FIG. 2 is a schematic side view of one embodiment of the catheter of FIG. 1, according to the invention.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. Optionally, the catheter 102 may define at least one flush port, such as flush port 210. The flush port 210 may be defined in the hub 204. The hub 204 may be configured and arranged to couple to the control module (104 in FIG. 1). In some embodiments, the elongated member 202 and the hub 204 are formed as a unitary body. In other embodiments, the elongated member 202 and the catheter hub 204 are formed separately and subsequently assembled together.

Figure 3:
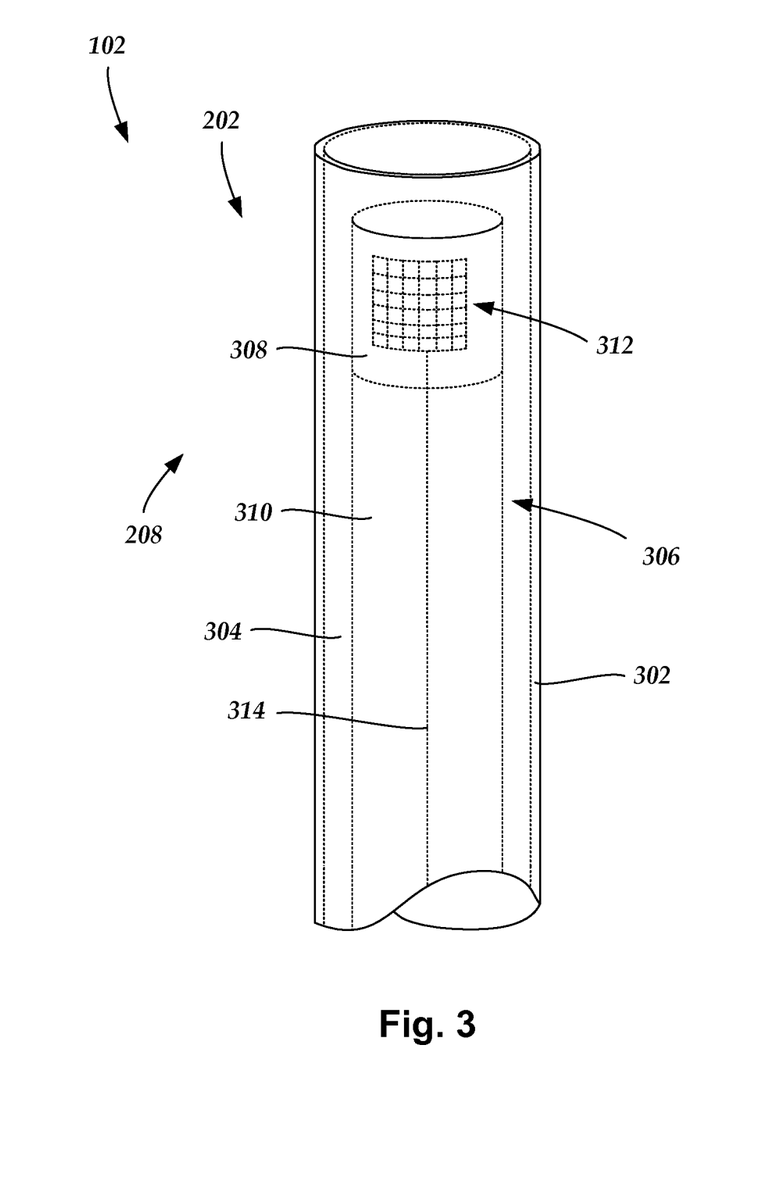
FIG. 3 is a schematic longitudinal cross-sectional view of one embodiment of a distal end of the catheter of FIG. 1 with an imaging device and a driveshaft disposed in a lumen of the catheter, according to the invention.

FIG. 3 is a schematic perspective view of one embodiment of the distal end 208 of the elongated member 202 of the catheter 102. The elongated member 202 includes a sheath 302 with a longitudinal axis 303 and a lumen 304. An imaging core 306 is disposed in the lumen 304. The imaging core 306 includes an imaging device 308 disposed in the catheter 102. In at least some embodiments, the imaging device 308 is coupled to a distal end of a driveshaft 310 (e.g., a rotatable driveshaft, or a non-rotatable driveshaft). One or more transducers 312 may be mounted to the imaging device 308 and employed to transmit and receive acoustic signals. The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

In a preferred embodiment (as shown in FIG. 3), an array of transducers 312 is mounted to the imaging device 308. In alternate embodiments, a single transducer may be employed. Any suitable number of transducers 312 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used. When a plurality of transducers 312 are employed, the transducers 312 can be configured into any suitable arrangement including, for example, an annular arrangement, a rectangular arrangement, or the like.

The one or more transducers 312 may be formed from one or more known materials capable of transforming applied electrical pulses to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like. Other transducer technologies include composite materials, single-crystal composites, and semiconductor devices (e.g., capacitive micromachined ultrasound transducers ("cMUT"), piezoelectric micromachined ultrasound transducers ("pMUT"), or the like).

The pressure distortions on the surface of the one or more transducers 312 form acoustic pulses of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic signals of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a conductive acoustic lens and a conductive backing material formed from an acoustically absorbent material (e.g., an epoxy substrate with tungsten particles). During operation, the piezoelectric layer may be electrically excited by both the backing material and the acoustic lens to cause the emission of acoustic pulses.

The one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

The imaging core 306 may, optionally, be rotated about the longitudinal axis 303 of the catheter 102. As the imaging core 306 rotates, the one or more transducers 312 emit acoustic signals in different radial directions. When an emitted acoustic signal with sufficient energy encounters one or more medium boundaries, such as one or more tissue boundaries, a portion of the emitted acoustic signal is reflected back to the emitting transducer as an echo signal. Each echo signal that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic signals transmitted and the echo signals received. In at least some embodiments, the rotation of the imaging core 306 is driven by the drive unit 110 disposed in the control module (104 in FIG. 1). In alternate embodiments, the one or more transducers 312 are fixed in place and do not rotate. In which case, the imaging device 308 may, instead, be manually moved (translationally, rotationally, or both). Alternately, the driveshaft 310 may rotate a mirror that reflects acoustic signals to and from the fixed one or more transducers 312.

When the one or more transducers 312 are rotated about the longitudinal axis 303 of the catheter 102 emitting acoustic pulses, a plurality of images can be formed that collectively form a radial cross-sectional image of a portion of the region surrounding the one or more transducers 312, such as the walls of a blood vessel of interest and the tissue surrounding the blood vessel. The radial cross-sectional image can, optionally, be displayed on one or more displays 112. The at least one of the imaging core 306 can be either electronically or manually rotated. In alternate embodiments, a non-rotating array may be employed that scans a patient's anatomy without any rotation or other physical movement.

The imaging core 306 may also move longitudinally along the blood vessel within which the catheter 102 is inserted so that a plurality of cross-sectional images may be formed along a longitudinal length of the blood vessel. During an imaging procedure the one or more transducers 312 may be retracted (i.e., pulled back) along the longitudinal length of the catheter 102. The catheter 102 can include at least one telescoping section that can be retracted during pullback of the one or more transducers 312. In at least some embodiments, the drive unit 110 drives the pullback of the imaging core 306 within the catheter 102. The drive unit 110 pullback distance of the imaging core can be any suitable distance including, for example, at least 5 cm, 10 cm, 15 cm, 20 cm, 25 cm, or more. The entire catheter 102 can be retracted during an imaging procedure either with or without the imaging core 306 moving longitudinally independently of the catheter 102.

When the imaging core 306 is refracted while rotating, the images may collectively form a continuous spiral shape along a blood vessel. A stepper motor may, optionally, be used to pull back the imaging core 306. The stepper motor can pull back the imaging core 306 a short distance and stop long enough for the one or more transducers 306 to capture an image before pulling back the imaging core 306 another short distance and again capturing another image, and so on, either with or without being rotated.

The quality of an image produced at different depths from the one or more transducers 312 may be affected by one or more factors including, for example, bandwidth, transducer focus, beam pattern, as well as the frequency of the acoustic pulse. The frequency of the acoustic pulse output from the one or more transducers 312 may also affect the penetration depth of the acoustic pulse output from the one or more transducers 312. In general, as the frequency of an acoustic pulse is lowered, the depth of the penetration of the acoustic pulse within patient tissue increases. In at least some embodiments, the IVUS imaging system 100 operates within a frequency range of 5 MHz to 120 MHz.

One or more communication lines 314 can electrically couple the transducers 312 to the control module 104 (see e.g., FIG. 1). In which case, the one or more communication lines 314 may extend along a longitudinal length of the rotatable driveshaft 310.

The catheter 102 with one or more transducers 312 mounted to the distal end 208 of the imaging core 308 may be inserted percutaneously into a patient via an accessible blood vessel, such as the femoral artery, femoral vein, or jugular vein, at a site remote from the selected portion of the selected region, such as a blood vessel, to be imaged. The catheter 102 may then be advanced through the blood vessels of the patient to the selected imaging site, such as a portion of a selected blood vessel.

Figure 4:
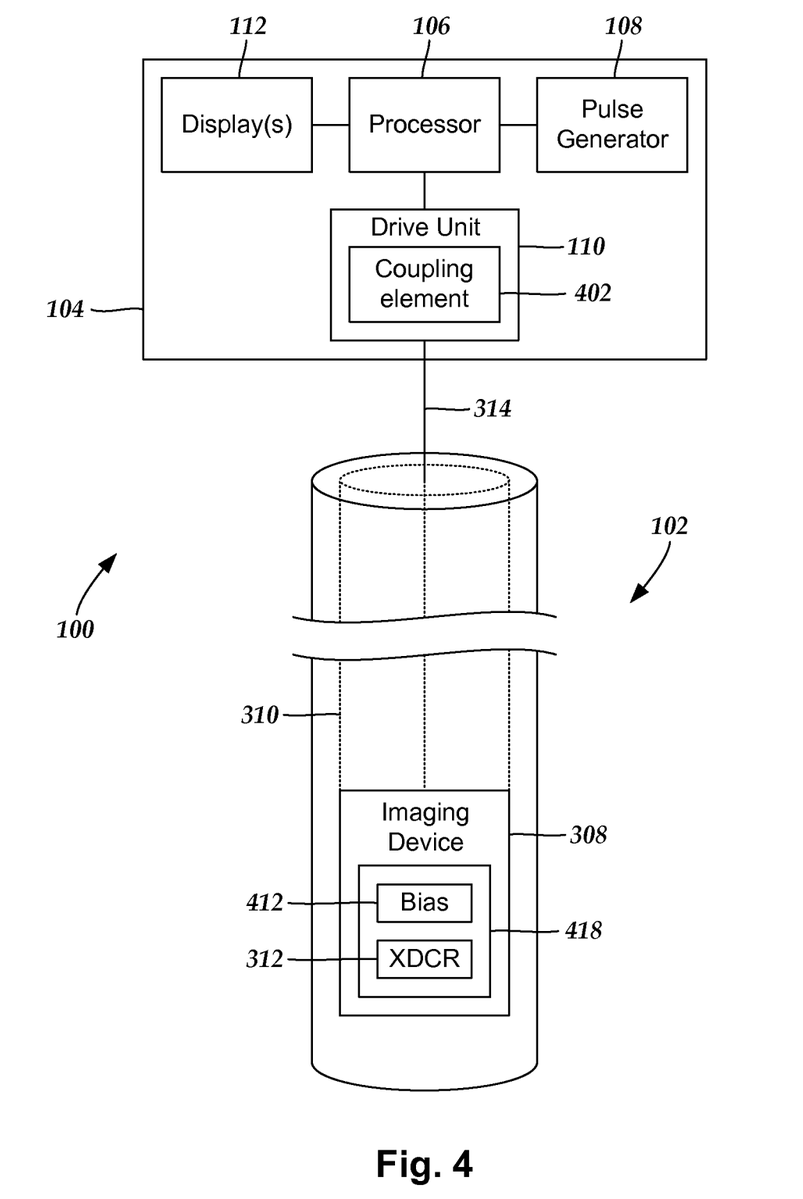
FIG. 4 is a schematic view of another embodiment of the imaging system of FIG. 1, the imaging system including a coupling element and an imaging device with bias circuitry, according to the invention.

Turning to FIG. 4, in at least some embodiments the system may include one or more inductive coupling elements, for example, for providing patient safety isolation, for coupling a stationary control module with a rotatable driveshaft, or the like or combinations thereof. The inductive coupling element may include, for example, a rotating transformer (e.g., a transformer with a stationary end and a rotating end). In the case of imaging devices that include semiconductor-based transducers, such as capacitive micromachined ultrasound transducers ("cMUT"), as well as other types of transducers, a constant bias voltage (e.g., a DC signal) may be needed, or desired, for operation. As described in more detail below, in some cases transmission of the bias signal to the imaging device may pose a problem because DC signals are not typically transmittable across inductive coupling elements.

FIG. 4 is a schematic view of another embodiment of the imaging system 100. The imaging system 100 includes the catheter 102 and the control module 104. The control module 104 includes the processor 106, the pulse generator 108, the one or more displays 112, and the drive unit 110. The catheter 102 includes one or more communication lines 314 and the driveshaft 310 coupling the imaging device 308 to the control module 104, via the drive unit 110. The imaging device 308 includes one or more transducers 312.

In the case of semiconductor-based transducers (e.g., cMUTs, MUTs, and the like), a constant bias voltage may be needed for operation. Additionally, at least some other types of ultrasound transducers may benefit when operated with a constant bias voltage. For example, single crystal piezoelectric transducers may lose their poling if unipolar (or bipolar) RF signals are applied. In which case, operating these transducers with a bias voltage may reduce or eliminate this issue. In cases where a bias voltage is provided to the one or more transducers 312, the imaging device 308 may include bias circuitry 412. In at least some embodiments, the one or more transducers 312 and the bias circuitry 412 are disposed on a shared semiconductor substrate 418, such as Silicon, Gallium Arsenide ("GaAs"), and the like.

In embodiments having a plurality of transducers 312, bias circuitry 412 can be configured to bias each individual transducer of the plurality of transducers 312, or multiple bias circuits 412 can be provided to bias each transducer separately. Although integration of the one or more transducers 312 and the bias circuitry 412 on the common substrate 418 is one possible arrangement, it will be understood that the systems and methods described herein are not limited to such. For instance, the one or more transducers 312 and the bias circuitry 412 can be fabricated as discrete components and packaged together, or fabricated and packaged discretely. Furthermore, the one or more transducers 312 and the bias circuitry 412 do not need to be physically housed together and can be positioned in any desired location within the catheter 102. For example, portions of the bias generating circuit may be disposed in one or more of the distal end of the catheter, the proximal end of the catheter, or the motor drive unit.

A coupling element 402 can be disposed in the drive unit 110 and coupled to a proximal end of the driveshaft 310. In at least some embodiments, the coupling element 402 is implemented as an inductive coupler (e.g., one or more rotating transformers, or the like) configured to transfer signals between the control module 104 and one or more communication lines 314. Although AC signals are commonly transmitted across inductive couplers, DC bias signals typically are not transmittable across inductive couplers.

As herein described, a bias signal may be applied to one or more transducers 312 of a medical imaging system, such as the IVUS imaging system 100. It will be understood that a bias signal can be used with other types of medical imaging systems, such as intracardiac echocardiography ("ICE") imaging systems. Examples of medical imaging systems with transducers that use bias voltages are found in, for example, U.S. Patent Application Publication No. 2006/0084875, which is incorporated herein by reference.

Figure 5:
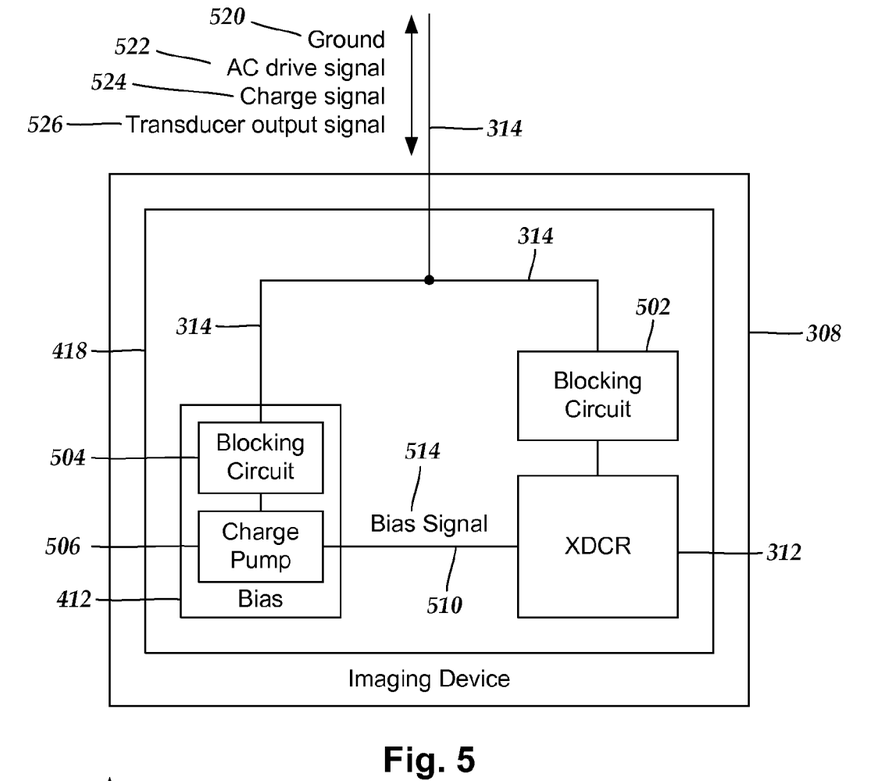
FIG. 5 is a schematic close-up view of one embodiment of the imaging device of FIG. 4, according to the invention.

FIG. 5 is a schematic view of one embodiment of the imaging device 308. In FIG. 5, the imaging device 308 includes the one or more transducers 312, the bias circuitry 412, and a first signal blocking circuit 502. In some instances, the one or more transducers 312, the bias circuitry 412, and the first signal blocking circuit 502 are all disposed on the substrate 418. As described above, the one or more communication lines 314 transmit signals between the control module 104 and the imaging device 308. The one or more communication lines 314 may include any number of signal lines, or transmission lines, as needed. For example, the one or more communication lines 314 may include a ground line for transmitting "ground" signals 520, one or more charge signal lines for transmitting charge signals 524, and one or more imaging lines for transmitting AC drive signals 522 and transducer output signals 526.

The "ground" signals 520 may be routed from the imaging device 308 to a ground (e.g., one or more portions of the control module 104, or the like). The charge signals 524 can be routed from the control module 104 to the bias circuitry 412 and used to generate a bias signal for the one or more transducers 312. The AC drive signals 522 can be routed from the control module 104 to the one or more transducers 312 and used to generate acoustic signals. The transducer output signals 526 can be routed from the one or more transducers 312 to the control module 104 and used to generate one or more medical images.

In at least some embodiments, the bias circuitry 412 includes a second signal blocking circuit 504 and one or more charge pumps 506. The second signal blocking circuit 504 can be used to route signals within the imaging device 308. For example, the second signal blocking circuit 504 can be used to block the AC drive signal 522 from propagating to the charge pump 506.

The one or more charge pumps 506 are configured and arranged to store charge signals 524 input along the one or more communication lines 314. The bias circuitry 412 is also configured and arranged to use the charge signals 524 stored in the one or more charge pumps 506 to form a bias signal 514 at a desired voltage level. The bias signal 514 can be output to the one or more transducers 312 along one or more bias signal lines 510. The design and implementation of the one or more charge pumps 506 are well known to those of skill in the art and any type of charge pump can be used. The one or more charge pumps 506 preferably include a charge storage unit, such as a switched capacitor bank, or the like.

The voltage levels of the bias signal 514 and the AC drive signal 522 are dependent on the needs of the application and the characteristics of each of the one or more transducers 312. In at least some embodiments, a larger bias signal 514 translates into the generation of a stronger acoustic signal. In addition, the bias signal 514 can also be a factor in determining the frequency of the generated acoustic signal. In some applications, the bias signal 514 can be approximately 100-150 volts, while the AC drive signal 522 can be 75 volts or more. It will be understood that these values are provided solely as examples and any signal levels can be used as desired.

In some embodiments where the coupling element 402 uses an inductive, or other non-physical electrical coupling, to transfer the AC drive signals 522 between the control module 104 and the imaging device 308, the charge signal 524 may be transmitted along the one or more communication lines 314 as a series of DC pulses that appear as an AC drive signal 522 to the coupling element 402. In at least some embodiments where the coupling element 402 uses a physical coupling, such as a brush/contact combination, the charge signal 524 can be a pure DC signal, if desired.

The signal blocking circuits 502 and 504 may be included to prevent unwanted interactions between the charge pump circuit 506 and the transducer 312. For example, the first signal blocking circuit 502 may be used to prevent a low frequency charging signal from being directly applied to the transducer 312 while a second blocking circuit 504 may prevent the charge pump circuit 506 from loading down the imaging signal.

Any suitable type of rectification circuitry can be used, such as one or more diodes, or the like. One of skill in the art will readily recognize that FIG. 5 depicts one of many possible different circuit layouts for the imaging device 308 and, accordingly, the systems and methods described herein are not limited to any one layout or circuit design.

Figure 6:
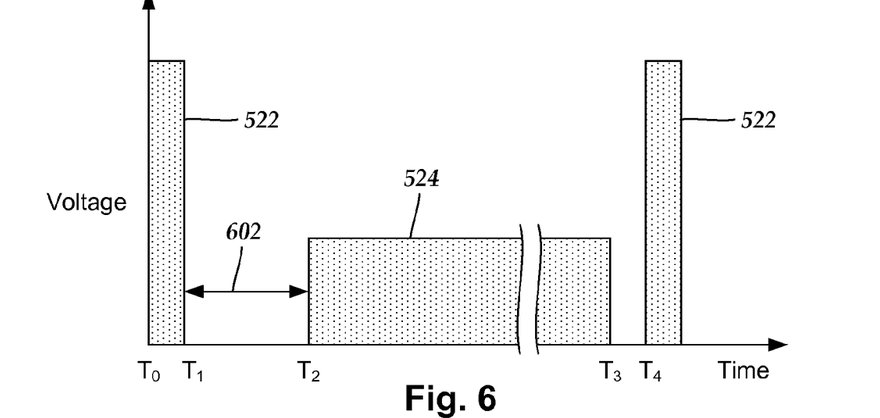
FIG. 6 is one embodiment of an exemplary timing diagram depicting signals being output from the control module of FIG. 4 to the imaging device of FIG. 4 over time, according to the invention.

Turning to FIG. 6, as mentioned above the one or more communication lines 314 may include any number of signal lines, or transmission lines, as needed. However, because the imaging system 100 is preferably used for intravascular applications, the width of catheter 102 can be a limiting factor preventing advancement through narrow vasculature. Thus, because each additional signal line generally adds width to the driveshaft 310, even if the driveshaft 310 itself is used as a signal line, it may be desirable to reduce the number of signal lines used in the imaging system 100.

In at least some embodiments, the imaging system 100 uses two communication lines 314 (e.g., a twisted pair of communication lines 314), which can be used to transfer single-ended or differential signals. In order to use two signal lines to transfer the "ground" signal 520, the AC drive signal 522, the charge signal 524, and the transducer output signal 526, in at least some embodiments the imaging system 100 uses a segmented timing regime.

FIG. 6 is one embodiment of an exemplary timing diagram depicting signals being output from the control module 104 over time. The transmission of an ultrasound pulse followed by the reception of the resulting echo signals is referred to herein as an imaging cycle. The imaging system 100 can be configured to perform a predetermined number of imaging cycles for every rotation, with each imaging cycle being performed at a separate angular location, or range of angular locations. For instance, in some embodiments, the imaging device 308 performs 360 imaging cycles in each rotation; with one imaging cycle being performed at an angular location located one degree apart.

Preferably, the imaging device 308 is rotated at a rate such that the time required to perform an imaging cycle is less than the time required to rotate the imaging device 308 from one angular location to the next. For example, in FIG. 6, at time $T_0$ the imaging device 308 is at a first angular location and at time $T_4$ the imaging device 308 has been rotated to a second angular position. The imaging cycle for the first angular location occurs between times $T_0$ and $T_2$. More specifically, the AC drive signal 522 is transmitted from control module 104 to the one or more transducers 312 from time $T_0$ to time $T_1$ in order to cause each individual transducer of the one or more transducers 312 to transmit an acoustic signal. From time $T_1$ to time $T_2$, the control module 104 is in a receiving period 602 awaiting any echo signals reflected by patient tissue in response to transmitted acoustic signals. This leaves the remaining time from $T_2$ to $T_4$ unused in any imaging cycle.

During the time from $T_2$ to $T_3$, the control module 104 preferably transmits the charge signal 524 to the bias circuitry 412. At time $T_4$, the control module 104 transmits another AC drive signal 522 to initiate another imaging cycle at the next angular location. In one narrow example embodiment, the time period from $T_0$ to $T_4$ is 130 microseconds, with the time period from $T_0$ to $T_1$ being approximately 50 nanoseconds, the time period from $T_1$ to $T_2$ being approximately 20 microseconds, and the time period from $T_2$ to $T_3$ being approximately 100 microseconds. These times are included as examples only and in no way limit the systems and methods described herein.

The amplitude of the charge signal 524 is preferably lower than an excitement threshold for the one or more transducers 312, where the one or more transducers 312 generate an acoustic signal (e.g., produce an ultrasound pulse). In some applications, small ultrasound pulses may be tolerable if, for instance, the small acoustic signal does not interfere with the subsequent imaging cycle.

The term "excitement threshold" as used herein, refers to the signal level which causes one or more transducers 312 to generate acoustic signals at a level sufficient to interfere with an imaging cycle. In one embodiment, the excitement threshold can be 75 volts and the charge signal 524 is maintained at 70 volts, while the AC drive signal 522 is 125 volts. These values are solely for example and in no way limit the systems and methods described herein. As mentioned above, the charge signal 524 can be a series of DC pulses instead of a continuous DC signal in order to propagate through coupling element 402, if needed. Also, it will be understood that any waveforms can be used for the AC drive signal 522 and the charge signal 524.

The generation of the charge signal 524 and the AC drive signal 522, as well as the proper timing for doing so, can be controlled by the control module 104. In at least some embodiments, the bias circuitry 412 is configured to limit the charge build up so that the charge signal 524 does not cause the bias circuitry 412 to apply the bias signal 514 at a voltage level that is excessively high. This can be performed through voltage limiting circuitry well known to those of skill in the art. Also, in certain applications, multiple charging cycles may be needed before the bias circuitry 412 can apply the proper voltage to the bias signal 514. Alternatively, in another embodiment the control module 104 can be configured to output the charge signal 524 prior to the commencement of imaging in order to charge up, or initialize, the bias circuitry 412. In which case, the length of the initialization period can be as long as needed to charge the bias circuitry 412. Preferably, the bias circuitry 412 is designed to be low leakage so that once the proper bias signal 514 voltage is reached, minimal subsequent charging is needed.

Figure 7:
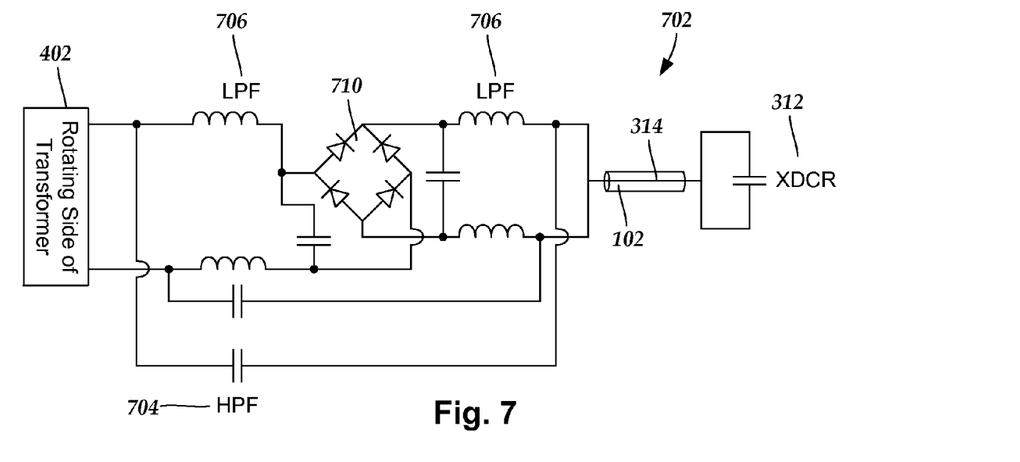
FIG. 7 is an electrical circuit diagram illustrating one embodiment of an electrical circuit suitable for use with the imaging system of FIG. 4, according to the invention.

Turning to FIG. 7, in at least some instances the coupling element 402 is an inductive coupler, such as one or more rotational transformers. In at least some embodiments, the one or more rotational transformers are magnetic transformers with stationary windings on the control module 104 side and rotating windings on the driveshaft 310 side. Suitable rotational transformers typically are designed to handle a spectrum of radio frequencies (e.g., approximately 1 MHz to 120 MHz) to handle various imaging modalities.

As mentioned above, the transducer output signals 526 are processed to form medical images. These signals 526 may be low level signals compared to the charge signals 524 and the AC drive signals 522. Ultrasound imaging systems are typically constructed to be very sensitive to the low level signals associated with the transducer output signals 526. Consequently, it may be a concern of system designers to not introduce additional signals that might interfere with these transducer output signals 526.

The AC drive signals 522 are typically transmitted at a desired frequency. This frequency is often at least 5 MHz, and no greater than 120 MHz. The transducer output signals 526 may be within an imaging frequency range centered at the frequency of the AC drive signal 522. In some cases, the imaging frequency range may be +/−10% of the frequency of the AC drive signal 522. In some cases, the imaging frequency range may be +/−5% of the frequency of the AC drive signal 522. In some cases, the imaging frequency range may be +/−8 MHz, 7 MHz, 6 MHz, 5 MHz, 4 MHz, 3 MHz, 2 MHz, 1 MHz, from the frequency of the AC drive signal 522.

In at least some embodiments, the charge signal 524 is transmitted across the inductive coupling element 402 using various types of AC signals. Once across the inductive coupling element 402, the charge signal 524 may be filtered and passed through a rectifier. In some cases, the rectified charge signal 524 can be applied directly to the one or more transducers 312. In other cases, the rectified charge signal 524 can be applied to the charge pump 506, and subsequently output to the one or more transducers 312, as described above with reference to FIG. 5. In some cases, the filters and rectifier are disposed at a proximal end of the catheter 102. In other embodiments, at least one of the filters or the rectifier is disposed on, or in proximity to, the imaging device 108.

As herein described, the charge signal 524 can be transmitted across the inductive coupling element 402 in several different ways without introducing excessive noise that may interfere with the transducer output signal 526. In some embodiments, the charge signal 524 is transmitted across the inductive coupling element 402 at frequencies that are substantially higher or lower than the AC drive signal 522. In some embodiments, the charge signal 524 is transmitted across the inductive coupling element 402 in short bursts that are separated in time from the imaging interval, as described above with reference to FIG. 6. In some embodiments, the charge signal 524 is transmitted across a separate, dedicated inductive coupling element to provide an independent path for the charge signal 524.

In some embodiments, a combination of two or more of the above charge-signal-transmission techniques can be used. For example, in some embodiments the charge signal 524 is transmitted across the inductive coupling element 402 in short bursts that are separated in time from the imaging interval and that are formed at frequencies that are substantially higher or lower than the AC drive signal 522. In some embodiments, the charge signal 524 is not continuous, but rather is applied in short bursts during a portion of the imaging cycle when image data are not being collected (see e.g., FIG. 6).

FIG. 7 is one embodiment of an electrical circuit diagram 702 for the imaging system 100. AC drive signals 522 and charge signals 524 are received from the control module 104 via the coupling element 402 (e.g., a rotating transformer). In at least some embodiments, the charge signals 524 are transmitted across the coupling element 402 as AC signals and converted to DC signals by a rectifier 710. In some embodiments, the charge signals 524 are applied in short bursts during one or more portions of an imaging cycle, as described above in detail with reference to FIG. 6. In which case, the short bursts can be stored in the charge pump 506, as described in detail with reference to FIG. 5, and output to the one or more transducers 312 as the bias signal 514 at a desired bias voltage level.

In at least some embodiments, the charge signals 524 are input to the imaging circuit 702 at a substantially different frequency than the AC drive signals 522. For example, in at lease some embodiments, the AC drive signals 522 are at approximately 60 MHz, while the charge signals 524 are at a frequency that is no greater than 5 MHz, 4 MHz, 3 MHz, 2 MHz, or 1 MHz. It will be understood that the charge signal 524 can be at a frequency that is either substantially higher or substantially lower than the AC drive signals 522. In at least some embodiments, the charge signal 524 has a frequency that is high enough to prevent the charge-signal transducer 802 from producing audible acoustic ringing (e.g., no lower than 20 kHz).

In some embodiments, the charge signal 524 has a frequency that is at least 20 kHz and no greater than 500 kHz. In some embodiments, the charge signal 524 has a frequency that is at least 20 kHz and no greater than 400 kHz. In some embodiments, the charge signal 524 has a frequency that is at least 20 kHz and no greater than 300 kHz. In some embodiments, the charge signal 524 has a frequency that is at least 20 kHz and no greater than 200 kHz. In some embodiments, the charge signal 524 has a frequency that is at least 20 kHz and no greater than 100 kHz. In some embodiments, the charge signal 524 has a frequency that is at least 20 kHz and no greater than 50 kHz.

In some cases, such as when there are nonlinearities in the circuit, harmonics of the charge signal 524 may be generated. Such harmonics may potentially be at frequencies within the imaging frequency range of the transducer output signal 526. Therefore, in at least some embodiments, the charge signal 524 is formed at a frequency that is significantly below the frequency of the AC charge signal 522. In at least some embodiments, the charge signal 524 is formed at a frequency that is no greater than one, two, or three decades below the frequency of the transducer output signal 526.

In at least some embodiments, the charge signal 524 is formed at a frequency that is no greater than one, two, or three decades below the lowest frequency of the imaging frequency range of the transducer output signal 526. For example, if the lowest frequency of the imaging frequency range is approximately 5 MHz, then a corresponding two-decade-lower charge signal 524 would be no greater than 50 kHz.

Forming the charge signal 524 at a frequency that is no greater than two decades below the lowest frequency of the imaging frequency range of the transducer output signal 526 may ensure that, even if the charge signal 524 is clipped to the point where it is nearly a square wave, any generated harmonics that fall within the imaging frequency range will be at least as low as −40 dB from the carrier amplitude. It will be understood that this is not a constraint when the charge signal 524 has a frequency that is above the imaging frequency range because harmonics are always above the fundamental frequency. It will also be understood that further exclusion of the charge signal 524 from the lowest frequency of the imaging frequency range may also be obtained by turning on the charge signal 524 only during non-imaging portions of the imaging cycle, as discussed above with reference to FIG. 6.

The AC drive signal 522 is routed to the one or more transducers 312, while the charge signal 524 is routed through the rectifier 710 to convert the charge signal 524 from AC to DC. Routing can be performed by any suitable technique including, for example, using one or more high pass filters 704, or one or more low pass filters 706, or both. In FIG. 7, the low pass filters 704 are disposed on both ends of the rectifier 710 so that the charge signal 524 is transmitted through the rectifier 710 prior to reaching the one or more transducers 312, while the AC drive signal 522 is routed around the rectifier 710. As discussed above, the charge signal 524 may be stored in the charge pump 506 subsequent to transmitting through the rectifier 710. In which case, the charge signal 524 can be routed to the one or more transducers 312 as the bias signal 514, as described above with reference to FIG. 5.

Figure 8A:
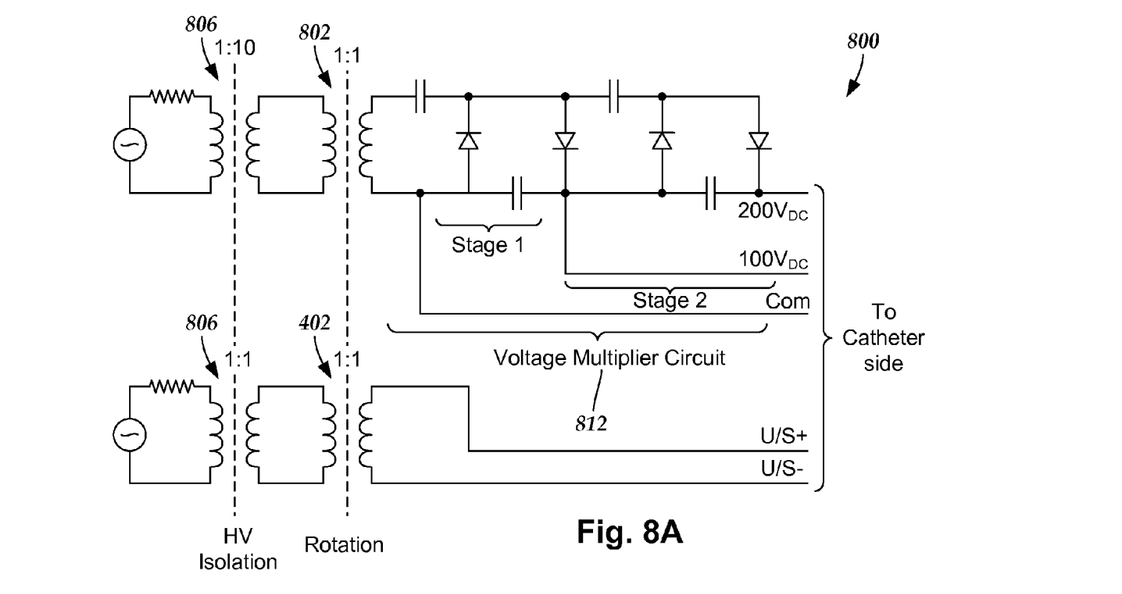
FIGS. 8A-8B are an electrical circuit diagram illustrating another embodiment of an electrical circuit suitable for use with the imaging system of FIG. 4, according to the invention.
Figure 8B:
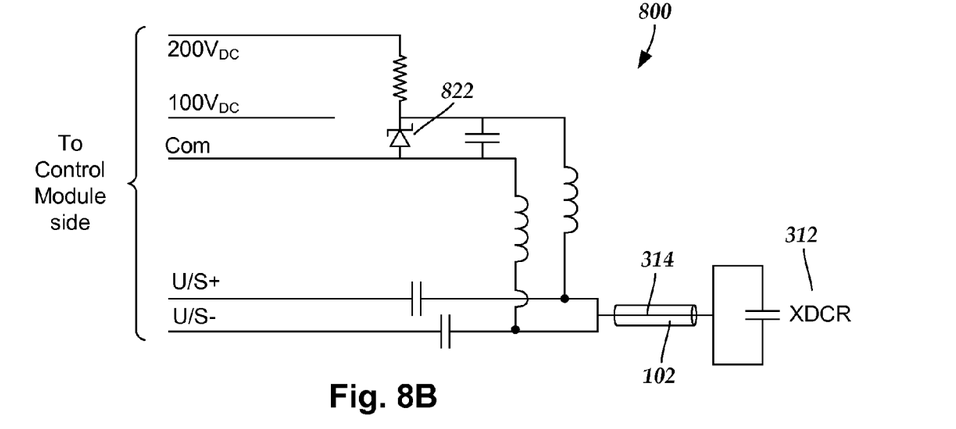

Turning to FIG. 8A, in at least some embodiments the charge signal 524 is transmitted from the control module 104 to the imaging device 308 via a dedicated charge-signal coupling element (e.g., a rotational transformer, or the like). FIGS. 8A-8B collectively show another embodiment of a medical imaging electrical diagram 800 for the imaging system 100. The medical imaging electrical diagram 800 includes a rotational transformer that is dedicated to the charge signal 524 and that is separate from the coupling element 402 used by the AC drive signal 522. In at least some embodiments, the rotational transformer 402 and the rotational transformer dedicated to the charge signal 524, are disposed in the drive unit 110 (see e.g., FIG. 4) or the proximal end of the catheter 102 (e.g., the hub), or both.

FIG. 8A shows a proximal end of the medical imaging electrical diagram 800, while FIG. 8B shows a distal end of the medical imaging electrical diagram 800. In FIG. 8A, the medical imaging electrical diagram 800 includes the coupling element 402, shown as a rotational imaging transformer, and a rotational charge-signal transformer 802. In at least some embodiments, one or more isolation transformers 806 may be included in series with one or more of the imaging transformer 402 and the charge-signal transformer 802. In some cases, a separate isolation transformer 806 may be disposed in series with each of the imaging transformer 402 and the charge-signal transformer 802. The isolation transformer(s) 806 can be used as a safety device to isolate the patient from high voltage electronics associated with the medical imaging system 100 or other equipment used in a medical procedure. It will be understood that, in at least some embodiments the system 100 includes one or more patient isolation transformers without including any rotating transformers.

The charge signal 524 can be provided to the imaging device 308 at any suitable voltage. In at least some embodiments, the charge signal 524 is no greater than 150V DC. In some cases, the one or more transducers 312 may not be able to tolerate voltages exceeding 200V DC. The voltage may be stepped up, as desired. In FIG. 8A, the isolation transformer 806 in series with the charge-signal transformer 802 is shown having a 1:10 voltage step-up. It will be understood that either isolation transformer 806 may have other voltage step-up values instead of a 1:10 voltage step-up.

In at least some embodiments, the medical imaging electrical diagram 800 includes a voltage multiplier circuit 812. The voltage multiplier circuit 812 may be used to provide an extra multiplication factor needed to increase the voltage of the charge signal 524. A voltage increase may be needed, for example, in situations where the combination of the input oscillator voltage and any voltage step-up realized in the charge-signal transducer 802, or the isolation transformer 806 in series with the charge-signal transducer 802, does not generate a sufficiently-high enough voltage for a particular transducer application.

FIG. 8B is one embodiment of a distal portion of the medical imaging electrical diagram 800. The medical imaging electrical diagram 800 includes one or more voltage regulators (e.g., one or more Zener diodes, one or more resistive voltage dividers, active regulator circuits, or combinations thereof) 822 for regulating the voltage of the charge signal 524. Using one or more voltage regulators 822 may reduce susceptibility to variations in parameters that might affect the voltage level of the charge signal 524.

Figure 9:
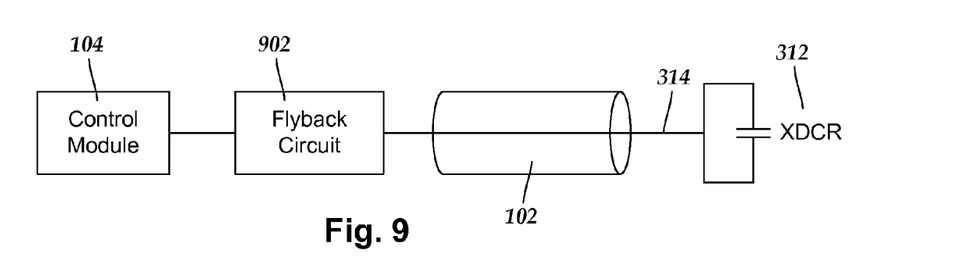
FIG. 9 is a schematic view of another embodiment of the imaging system of FIG. 4, the imaging system including a flyback circuit, according to the invention.

Turning to FIG. 9, in some embodiments the charge signal 524 is transmitted across a flyback circuit. FIG. 9 is a schematic view of one embodiment of an imaging system that includes a flyback circuit 902. The flyback circuit 902 can be electrically coupled to the one or more communication lines 314. In some cases, the flyback circuit 902 is disposed in a proximal end of the catheter 102. In alternate embodiments, the flyback circuit is disposed on the control module 104.

The flyback circuit 902 may include a driver circuit for establishing a DC current in a primary winding of a rotating transformer. The DC current input to the rotating transformer can be interrupted suddenly. The tendency of the inductance of the primary winding is to maintain the flow of current, despite the current being suddenly interrupted. Consequently, the interrupted current causes a voltage to develop across the inductor. If a secondary winding is coupled to the primary winding, a "flyback" voltage also appears across the secondary winding. The "flyback" voltage appearing across the secondary winding can be input the charge pump (506 in FIG. 5), as described above with reference to FIG. 5. In at least some embodiments, the flyback cycles can be interleaved with imaging cycles in such a way that they would not interfere with imaging, as described above with reference to FIG. 6. Optionally, the flyback circuit 902 may be used in conjunction with one or more of a rectifier, a voltage regulator, and a DC combiner circuit, as described above. In at least some imaging systems, high voltage RF transmitter pulses are provided by MOSFET (or similar) switches that may also provide the current, and the rapid interruption of the current, needed to produce a flyback voltage.

Figure 10:
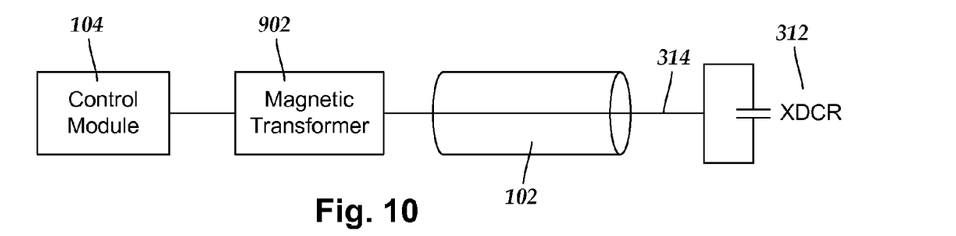
FIG. 10 is a schematic view of yet another embodiment of the imaging system of FIG. 4, the imaging system including a magnetic transformer, according to the invention.

Turning to FIG. 10, in some embodiments, the charge signal 524 is transmitted across a magnetic rotary transformer as a series of square pulses. In at least some embodiments, the square pulses act as a pedestal voltage for the imaging signal. FIG. 10 is a schematic view of one embodiment of an imaging system that includes a magnetic transformer 1002 suitable for conveying square pulses. The magnetic transformer 1002 can be electrically coupled to the one or more communication lines 314. In some cases, the magnetic transformer 1002 is disposed in a proximal end of the catheter 102. In alternate embodiments, the magnetic transformer 1002 is disposed on the control module 104.

Magnetic transformers are capable of conveying square pulses so long as the duration of the pulse is short compared to the time constant produced by the transformer primary inductance and the resistive impedances driving and terminating the transformer. Thus, if an RF transmit signal is generated to provide a high frequency ultrasound waveform superposed on a charge signal formed as a square pedestal pulse, and the duration of the charge signal is much shorter than the time constant of the RF transmit signal, then both the RF transmit signal and a corresponding charge signal can be transmitted to the one or more transducers 312. Optionally, one or more diodes, one or more capacitors, one or more regulators, or the like or combinations thereof can be used to maintain the charge signal during the receive intervals ($T_1$ to $T_2$) of an imaging cycle, as described above with reference to FIG. 6.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A medical imaging system, comprising:
    a catheter configured and arranged for insertion into an intravascular portion of a living being, the catheter having a distal end and a proximal end, the catheter defining a lumen;
    an imaging device disposed in the lumen of the catheter, the imaging device for imaging interior portions of the living being, the imaging device comprising:

at least one ultrasound transducer, and
bias circuitry electrically coupled to the at least one transducer and configured and arranged to electrically bias the at least one transducer;
at least one communication line coupled to both the at least one ultrasound transducer and the bias circuitry and extending to a proximal end of the catheter, the at least one communication line configured and arranged for transmitting a transducer drive signal to the at least one transducer, and transmitting a charge signal to the bias circuitry; and
at least one inductive coupler in communication with the at least one communication line;
wherein the transducer drive signal and the charge signal are both AC signals, the transducer drive signal having a transducer-drive-signal frequency in a range of 5 MHz to 120 MHz, and the charge signal having a charge-signal frequency in a range of 20 kHz to 500 kHz;
wherein the AC charge signal is transmitted along the at least one communication line through the at least one inductive coupler;
the imaging device further comprising a first blocking circuit disposed between the ultrasound transducer and the at least one inductive coupler, the first blocking circuit comprising a high pass filter configured and arranged to pass the transducer drive signal to the ultrasound transducer and to block the charge signal; and
a second blocking circuit disposed between the bias circuitry and the at least one inductive coupler, the second blocking circuit comprising a low pass filter configured and arranged to pass the charge signal to the bias circuitry and to block the transducer drive signal.

2. The system of claim 1, wherein the at least one inductive coupler comprises an isolation transformer.

3. The system of claim 1, further comprising a control module communicatively coupled with the imaging device via the at least one communication line, the control module comprising
a pulse generator configured and arranged for providing the transducer drive signal and the charge signal to the imaging device,
a processor configured and arranged for processing received transducer output signals from the at least one transducer, and
a display coupled to the processor.

4. The system of claim 3, wherein the control module is configured and arranged to output the transducer drive signal during a first time period and the control module is configured and arranged to output the charge signal during a second time period that does not overlap in time with the first time period.

5. The system of claim 3, wherein the at least one inductive coupler comprises a first rotating transformer disposed between the control module and the at least one communication line.

6. The system of claim 5, wherein the transducer drive signal is transmitted along the at least one communication line through the first rotating transformer.

7. The system of claim 5, further comprising a flyback circuit coupled to the first rotating transformer, the flyback circuit configured and arranged for generating a flyback voltage.

8. The system of claim 5, wherein the at least one inductive coupler comprises a second rotating transformer disposed between the control module and the at least one communication line, and wherein the charge signal is transmitted along the at least one communication line through the second rotating transformer.

9. The system of claim 3, further comprising a rotatable driveshaft configured and arranged for insertion into the lumen of the catheter, wherein the imaging device is coupled to the driveshaft.

10. The system of claim 9, wherein the control module further comprises a motor drive unit configured and arranged to control rotational and translational movement of the driveshaft within the lumen of the catheter.

11. The system of claim 9, wherein the control module is configured and arranged to output the transducer drive signal during a first time period and the control module is configured and arranged to output the charge signal during a second time period that does not overlap in time with the first time period.

12. The system of claim 1, wherein the charge-signal frequency is less than the transducer-drive-signal frequency.

13. The system of claim 12, wherein the charge-signal frequency is no greater than two decades below the transducer-drive-signal frequency.

14. The system of claim 1, wherein the at least one communication line is configured and arranged for transmitting a transducer output signal to the at least one transducer, the transducer output signal having an imaging frequency range centered around the transducer-drive-signal frequency.

15. The system of claim 14, wherein the charge-signal frequency is no greater than two decades below a lowest frequency of the imaging frequency range.

16. The system of claim 1, wherein the system further comprises a rectification circuit for converting the AC charge signal input from the at least one communication line to a DC charge signal.

17. The system of claim 16, wherein the system further comprises a charge pump for storing DC charge signals input from the rectification circuitry and forming a bias signal to electrically bias the at least one transducer.

18. The system of claim 1, wherein the system further comprises a voltage multiplier configured and arranged for increasing the voltage of the charge signal.

19. The system of claim 1, wherein the system further comprises a voltage regulator configured and arranged for regulating the voltage of the charge signal.

20. The system of claim 1, wherein the charge signal has a square waveform.

21. A medical imaging system, comprising:
a catheter configured and arranged for insertion into an intravascular portion of a living being, the catheter having a distal end and a proximal end, the catheter defining a lumen;
an imaging device disposed in the catheter, the imaging device for imaging interior portions of the living being, the imaging device comprising:
at least one ultrasound transducer, and
bias circuitry electrically coupled to the at least one transducer and configured and arranged to electrically bias the at least one transducer;
a control module communicatively coupled with the imaging device, the control module configured and arranged to generate a transducer drive signal and a charge signal, the transducer drive signal having a transducer-drive-signal frequency in a range of 5 MHz to 120 MHz, and the charge signal having a charge-signal frequency in a range of 20 kHz to 500 kHz;
at least one communication line coupling the control module to both the at least one ultrasound transducer and the bias circuitry, the at least one communication line configured and arranged for transmitting the transducer drive signal and the charge signal to the imaging device, wherein the transducer drive signal and the charge signal are both AC signals;

a first rotating transformer disposed between the control module and the at least one communication line, the first rotating transformer configured and arranged to receive the transducer drive signal;

a second rotating transformer disposed between the control module and the at least one communication line, the second rotating transformer configured and arranged to receive the charge signal;

a first blocking circuit disposed between the at least one ultrasound transducer and the first rotating transformer, the first blocking circuit comprising a high pass filter configured and arranged to pass the transducer drive signal to the ultrasound transducer and to block the charge signal; and a second blocking circuit disposed between the bias circuitry and the second rotating transformer, the second blocking circuit comprising a low pass filter configured and arranged to pass the charge signal to the bias circuitry and to block the transducer drive signal.

22. A method of intravascular ultrasound imaging with an image processing system, comprising:

transmitting an AC transducer drive signal from a pulse generator through at least one inductive coupler to at least one transducer disposed at a distal end of a medical device insertable into patient vasculature, wherein the AC transducer drive signal comprises a plurality of frequencies within an imaging frequency band centered in a range of 5 MHz to 120 MHz and wherein the AC transducer drive signal is configured and arranged to cause the at least one transducer to transmit an acoustic signal;

transmitting an AC charge signal from the pulse generator to bias circuitry disposed at the distal end of the medical device, the AC charge signal having a charge-signal frequency in a range of 20 kHz to 500 kHz, the bias circuitry communicatively coupled to the at least one transducer, wherein the AC charge signal comprises a charge-signal frequency that does not overlap with the imaging frequency band, the image processing system further comprising a first blocking circuit disposed between the at least one ultrasound transducer and the at least one inductive coupler, the first blocking circuit comprising a high pass filter configured and arranged to pass the AC transducer drive signal to the ultrasound transducer and to block the AC charge signal, and a second blocking circuit disposed between the bias circuitry and the at least one inductive coupler, the second blocking circuit comprising a low pass filter configured and arranged to pass the AC charge signal to the bias circuitry and to block the AC transducer drive signal;

converting the AC charge signal to a DC charge signal;

storing the DC charge signal in a charge pump;

transmitting a bias signal to the at least one transducer, the bias signal formed from the stored DC charge signal; and transmitting at least one acoustic signal from the at least one transducer.

23. The method of claim 22, wherein transmitting the AC transducer drive signal from the pulse generator comprises transmitting the AC transducer drive signal from the pulse generator during a first time period, and wherein transmitting the AC charge signal from the pulse generator comprises transmitting the AC charge signal from the pulse generator during a second time period that does not overlap in time with the first time period.

24. The method of claim 22, wherein transmitting the AC transducer drive signal from the pulse generator comprises transmitting the AC transducer drive signal through a first rotating transformer.

25. The method of claim 24, wherein transmitting the AC charge signal from the pulse generator through at least one inductive coupler comprises transmitting the AC charge signal through a second rotating transformer.

26. The method of claim 22, further comprising rotating the at least one transducer.

27. The method of claim 26, wherein transmitting the AC transducer drive signal from the pulse generator comprises transmitting the AC transducer drive signal from the pulse generator during a first time period, and wherein transmitting the AC charge signal from the pulse generator comprises transmitting the AC charge signal from the pulse generator during a second time period that does not overlap in time with the first time period.

* * * * *